United States Patent [19]

Hope et al.

[11] Patent Number: 5,420,373
[45] Date of Patent: May 30, 1995

[54] CONTROLLED FORMATION OF OLEFIN OLIGOMERS

[75] Inventors: Kenneth D. Hope; Ting C. Ho; Barrett L. Cupples, all of Kingwood, Tex.

[73] Assignee: Chevron Chemical Company, San Francisco, Calif.

[21] Appl. No.: 217,265

[22] Filed: Mar. 24, 1994

[51] Int. Cl.$^6$ .............................................. C07C 2/08
[52] U.S. Cl. ................................ 585/525; 585/502; 585/510; 585/520
[58] Field of Search ................ 585/502, 510, 525, 520

[56] References Cited

U.S. PATENT DOCUMENTS

| | | | |
|---|---|---|---|
| 3,769,363 | 10/1973 | Brennan | 260/683.15 B |
| 3,997,621 | 12/1976 | Brennan | 260/683.15 B |
| 4,218,330 | 8/1980 | Shubkin | 252/46.6 |
| 4,436,947 | 3/1984 | Morganson et al. | 585/525 |
| 4,910,355 | 3/1990 | Shubkin et al. | 585/255 |
| 4,982,026 | 1/1991 | Karn et al. | 585/18 |
| 5,068,487 | 11/1991 | Theriot | 585/510 |
| 5,171,905 | 12/1992 | Theriot et al. | 585/10 |
| 5,171,918 | 12/1992 | Shubkin et al. | 585/510 |

FOREIGN PATENT DOCUMENTS 323759 7/1989 European Pat. Off.

*Primary Examiner*—P. Achutamurthy
*Attorney, Agent, or Firm*—W. K. Turner; E. A. Schaal

[57] ABSTRACT

An oligomer is made by contacting a straight-chain, α-olefinic monomer with boron trifluoride and a hydroxy carbonyl promoter. The hydroxy carbonyl is preferably a β-hydroxy-ketone, such as 4-hydroxy-4-methyl-2-pentanone. A second promoter can be used in conjunction with the boron trifluoride and the hydroxy carbonyl promoter. Possible secondary promoters include aldehydes, alcohols, alcohol alkoxylates, carboxylic acids, ethers, ketones, and their mixtures. Preferably the oligomer product has a kinematic viscosity at 100° C. of less than 1.7 cSt; has a dimer to trimer and higher oligomer ratio of at least 1:1; and is at least 90 wt. % dimer and trimer of the monomer.

18 Claims, No Drawings

CONTROLLED FORMATION OF OLEFIN OLIGOMERS

The present invention relates to a process of producing dimers and trimers of olefins in significantly high yields.

BACKGROUND OF THE INVENTION

It is well known to make polyalphaolefins by reacting 1-decene with boron trifluoride and butanol. The oligomer product is a mixture of dimer, trimer, and higher molecular weight materials.

The market for the trimer and higher molecular weight materials is well established, both in military applications and in automotive and industrial uses that require a 4 centistokes (cSt) or greater kinematic viscosity. The dimer, which has a viscosity of about 2 cSt, was usually recycled to the reaction. That resulted in better economics but a somewhat poorer product performance. Because of the market demand for the trimer and higher molecular weight materials and lack of market demand for dimer production, most of the work in this area has involved minimizing the amount of dimers made.

The dimer is useful in heat transfer fluids, dielectric fluids, and lubricating fluids. Recently, it also has been found to be useful in drilling fluids. This involves replacing petroleum fractions, chiefly diesel oil, in oil-based drilling fluids with environmentally compatible polyalphaolefins. Oil-based drilling fluids are undesirable in off-shore petroleum exploration because those fluids produce an unwanted sheen on the water and are harmful to certain marine life. This new market for dimers has changed the economics of the industry. Now, there is an economic motivation to increase dimer yield, rather than minimize it.

U.S. Pat. Nos. 5,068,487; 5,171,905; and 5,171,918 disclose a process for producing predominately dimer and trimer. That process uses boron trifluoride in conjunction with alcohol alkoxylates

[RO(CHR'—CHR"O)$_n$—H].

Unfortunately, this process can create a highly viscous emulsion layer in the reactant and aqueous wash streams. These emulsions can cause operating difficulties, such as inhomogeneity in the reactor, process line plugging, poor product recovery, and lengthy phase separation times.

Other patents of interest are U.S. Pat. Nos. 3,769,363; 3,997,621; 4,218,330; 4,436,947; and 4,982,026.

U.S. Pat. No. 3,769,363 by Brennan discloses oligomerization of $C_6$–$C_{12}$ normal $\alpha$-olefins, such as 1-decene, with boron trifluoride and $C_5$ carboxylic acid to improve trimer yields.

U.S. Pat. No. 3,997,621 by Brennan discloses oligomerization of $C_6$–$C_{12}$ normal $\alpha$-olefins using alcohols or water promoters in conjunction with small amounts of methyl and ethyl esters of a $C_2$–$C_5$ mono carboxylic acid to improve trimer yields.

U.S. Pat. No. 4,218,330 by Shubkin discloses dimerization of a $C_{12}$–$C_{18}$ monomer with a boron trifluoride-water complex and an excess of boron trifluoride. The product is distilled to remove the monomer and is hydrogenated for use as a crankcase lubricant. This product is mainly dimers, with minor amounts of trimers and higher oligomers. However, the monomer conversion is unacceptably low.

U.S. Pat. No. 4,436,947 by Morganson et al. discloses oligomerization of $C_6$–$C_{20}$ olefins, such as 1-decene, with boron trifluoride and a mixture of an aliphatic alcohol, an aliphatic ketone, and a polyol. This product is predominately trimer.

U.S. Pat. No. 4,982,026 by Karn et al. discloses polymerization of lower alkene monomers ($C_2$–$C_6$) with boron trifluoride and a strong acid, such as phosphoric acid, to produce a polymer having a molecular weight from 250 to 500 and having a high vinylidene content. Besides having a degree of oligomerization greater than two, the process requires subzero reaction temperatures, which are uneconomical.

U.S. Pat. Nos. 3,769,363; 3,997,621; 4,218,330; 4,436,947; 4,982,026 5,068,487; 5,171,905; and 5,171,918 are hereby incorporated by reference for all purposes.

SUMMARY OF THE INVENTION

We have found a process of producing dimers and trimers in significantly high yields. In our process, an olefinic monomer is contacted with boron trifluoride and a hydroxy carbonyl promoter. The term "hydroxy carbonyl" includes both hydroxy ketones and hydroxy aldehydes. The type and composition of the promoter play important roles in obtaining the best product distribution.

Preferably, the hydroxy carbonyl is a hydroxy ketone. Preferably the hydroxyl group is attached to an alkyl group having 1–6 carbon atoms with the alkyl group being either straight or branched. Preferably the ketone group is either methyl ketone or ethyl ketone.

Preferably, the hydroxy ketone is either hydroxy acetone, 1-hydroxy-2-butanone, 3-hydroxy-2-butanone, 3-hydroxy-3-methyl-2-butanone, or 4-hydroxy-4-methyl-2-pentanone (also known as diacetone alcohol). More preferably, it is 4-hydroxy-4-methyl-2-pentanone. Compounds found particularly useful in this invention are $\alpha$-hydroxy ketones and $\beta$-hydroxy ketones.

A secondary promoter can be used in conjunction with the boron trifluoride and the hydroxy carbonyl promoter. Examples of such secondary promoters include aldehydes, alcohols, alcohol alkoxylates, carboxylic acids, ethers, ketones, and their mixtures. Preferably, this secondary promoter is methanol.

The olefinic monomer is preferably a straight-chain, $\alpha$-olefinic monomer containing from 6 to 20 carbon atoms, more preferably from 6 to 12 carbon atoms. The oligomer product from a $C_6$–$C_{12}$, straight-chain, $\alpha$-olefinic monomer preferably has a kinematic viscosity at 100° C. of less than 3.6 cSt.

Still more preferably, the olefinic monomer contains predominately 8 to 10 carbon atoms. The oligomer product from such a monomer preferably has a kinematic viscosity at 100° C. of less than 2.0 cSt., more preferably less than 1.7 cSt.

The oligomer product should be predominately dimer and trimer, and the dimer to trimer and higher oligomer ratio should be at least 0.5:1, more preferably at least 1:1.

Preferably, before removal of unreacted monomer, the oligomer product is at least 70 wt. % dimer and trimer. More preferably, it is at least 80 wt. % dimer and trimer. Most preferably, it is at least 90 wt. % dimer and trimer.

DETAILED DESCRIPTION OF THE INVENTION

In its broadest aspect, the present invention involves the oligomerization of an olefinic monomer by contacting that monomer with boron trifluoride and at least one hydroxy carbonyl promoter.

HYDROXY CARBONYL PROMOTER

By "hydroxy carbonyl," we mean an organic compound having both a hydroxyl group (containing an —OH unit) and a carbonyl group (containing a —C=O unit). As used herein, the term hydroxy carbonyl includes both hydroxy ketones and hydroxy aldehydes, but does not include carboxylic acids.

Preferably, the hydroxy carbonyl is a hydroxy ketone because of concerns of unavailability, odor, and instability of hydroxy aldehydes. Preferably the hydroxyl group is attached to an alkyl group having from 1 to 6 carbon atoms, with the alkyl group being either straight or branched. Preferably the ketone group is either methyl ketone or ethyl ketone.

The hydroxy carbonyl can have more than one hydroxyl group and can have more than one carbonyl group. The compounds can have alternating hydroxyl and carbonyl groups (e.g., 4-hydroxy-4-methyl-2,6-heptanedione), or similar groups can be grouped together (e.g., 6-hydroxy-6-methyl-2,4-heptanedione). Neither the hydroxyl groups nor the carbonyl groups have to be the same throughout the molecule. For instance, in a dione compound, the carbonyl groups could be both methyl-ketone and ethyl-ketone (e.g., 4-hydroxy-4-methyl-2,6-octanedione).

More than one hydroxy ketone can be used. For instance, in one preferred embodiment, 1-hydroxy-2-butanone and 4-hydroxy-4-methyl-2-pentanone are used together.

The ratio of hydroxyl groups to carbonyl groups is preferably 1:1, (e.g., 4-hydroxy-4-methyl-2-pentanone). That ratio can be higher or lower. For instance, other hydroxy ketones conceived to be part of this invention include 2,6-dihydroxy-2,6-dimethyl-4-heptanone (ratio of 2:1) and 4-hydroxy-4-methyl-2,6-heptanedione (ratio of 1:2).

Suitable hydroxy ketones include, but are not limited to, hydroxy acetone, 1-hydroxy-2-butanone, 3-hydroxy-2-butanone, 4-hydroxy-2-butanone, 3-hydroxy-3-methyl-2-butanone, 3-hydroxy-2-pentanone, 4-hydroxy-2-pentanone, 1-hydroxy-3-pentanone, 2-hydroxy-3-pentanone, 3-hydroxy-3-methyl-2-pentanone, 3-hydroxy-4-methyl-2-pentanone, 4-hydroxy-3-methyl-2-pentanone, 4-hydroxy-4-methyl-2-pentanone, 2-hydroxy-2-methyl-3-pentanone, 3-hydroxy-2-hexanone, 4-hydroxy-2-hexanone, 4-hydroxy-3-hexanone, 5-hydroxy-3-hexanone, 4-hydroxy-4-methyl-3-hexanone, 4-hydroxy-5-methyl-3-hexanone, 5-hydroxy-4-methyl-3-hexanone, 5-hydroxy-5-methyl-3-hexanone, 4-hydroxy-3-heptanone, and 5-hydroxy-3-heptanone.

Preferably, the hydroxyl group is attached to a tertiary carbon, such as in 3-hydroxy-3-methyl-2-butanone, 3-hydroxy-3-methyl-2-pentanone, 4-hydroxy-4-methyl-2-pentanone, 2-hydroxy-2-methyl-3-pentanone, 4-hydroxy-4-methyl-3-hexanone, 5-hydroxy-5-methyl-3-hexanone. Of these hydroxy ketones, the preferred hydroxy ketones are β-hydroxy ketones, such as 4-hydroxy-4-methyl-2-pentanone and 5-hydroxy-5-methyl-3-hexanone.

A preferred hydroxy carbonyl is 4-hydroxy-4-methyl-2-pentanone because it gives no emulsion in the reactor or in the water wash, as discussed below. 1-hydroxy-2-butanone gives a slight emulsion in the water wash and hydroxy acetone gives a significant emulsion in the water wash. In general, we have found that tertiary hydroxy ketones, such as, 4-hydroxy-4-methyl-2-pentanone and 3-hydroxy-3-methyl-2-butanone form no, or appreciably lesser amounts of, emulsion than secondary or primary hydroxy ketones. Secondary hydroxy ketones, such as, 3-hydroxy-2-butanone appear to form more dimer than the corresponding primary hydroxy ketones, such as, 1-hydroxy-2-butanone. Also, higher conversion rates have been observed with α-hydroxy ketones versus β-hydroxy ketones.

SECONDARY PROMOTERS

In one embodiment, a second promoter can be used in conjunction with the boron trifluoride and the hydroxy carbonyl promoter. Possible secondary promoters include aldehydes, alcohols, alcohol alkoxylates, carboxylic acids, ethers, ketones, and their mixtures. These secondary promoters are used to further initiate oligomerization.

Preferably an alcohol, such as methanol, is used as a secondary promoter to achieve a faster reaction rate. The amount of alcohol or alcohol alkoxylate used depends, in part, on the ratio of hydroxyl groups to carbonyl groups in the hydroxy carbonyl. Less secondary promoter is needed if this ratio is high (i.e., if there is an excess of hydroxyl groups to carbonyl groups).

Alcohol alkoxylates useful as secondary promoters can be represented, for example, by the formula:

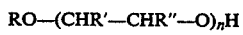

RO—(CHR'—CHR"—O)$_n$H where R is hydrocarbyl containing from 1 to 24 carbons, including mixtures thereof, R' and R" are independently hydrogen, methyl, or ethyl, and n averages 1 to 15. Such alcohol alkoxylates are disclosed in U.S. Pat. No. 5,068,487, entitled "Olefin Oligomerization With BF$_3$ Alcohol Alkoxylate Co-Catalysts," which is hereby incorporated by reference for all purposes.

A ketone, such as methyl-ethyl-ketone, can also be used as a secondary promoter to suppress the formation of higher oligomers.

OLEFINIC MONOMER

Preferably, olefins used in making the oligomer are predominately (at least 50 mole %) C$_6$–C$_{20}$ straight-chain, mono-olefinically unsaturated hydrocarbons in which the olefinic unsaturation occurs at the 1- or α-position of the straight carbon chain. Straight-chain α-olefins are preferred because they are more reactive and commercially available. Such α-olefins can be made by the thermal cracking of paraffinic hydrocarbons or by the well known Ziegler ethylene chain growth and displacement on triethyl aluminum. Individual olefins may be used, as well as mixtures of such olefins. Examples of such olefins are 1-hexene, 1-heptene, 1-octene, 1-nonene, 1-decene, 1-dodecene, 1-hexadecene and 1-tetradecene. The more preferred normal-α-olefin monomers are those containing about 6 to 12 carbon atoms. The most preferred olefin monomers are 1-octene, 1-decene, and mixtures thereof. The olefin monomers can also contain minor amounts of up to about 50 mole %, and usually less than 25 mole %, of internal olefins and vinylidene olefins.

OLIGOMER PRODUCT

The oligomer product is that portion of the reaction product remaining after boron trifluoride, hydroxy carbonyl promoters, secondary promoters, and unreacted monomer are removed. When the olefinic monomer contains predominately 6 to 12 carbon atoms, the oligomer product preferably has a kinematic viscosity at 100° C. of less than 3.6 cSt. Preferably, the olefinic monomer contains predominately 8 to 10 carbon atoms, the oligomer product preferably has a kinematic viscosity at 100° C. of less than 2.0 cSt, more preferably less than 1.7 cSt.

Preferably, the oligomer product is predominately the dimer and trimer of the monomer. More preferably, at least 70 wt. % of the oligomer product is dimer and trimer before removal of unreacted monomer. Still more preferably, at least 80 wt. % of the oligomer product is dimer and trimer before removal of unreacted monomer. Most preferably, at least 90 wt. % of the oligomer product is dimer and trimer before removal of unreacted monomer.

Preferably, the dimer to trimer and higher oligomer ratio is at least 0.5:1. The dimer to trimer and higher oligomer ratio is the weight ratio of dimer to the sum of trimer and higher oligomers. More preferably, that ratio is at least 1:1.

OLIGOMERIZATION REACTION

The hydroxy carbonyl promoter and secondary promoters are used in minor but effective amounts. For example, the total amount of promoter used can be from about 0.001 to 0.04 moles per mole of monomer (0.1 to 4.0 mole percent). In general, the boron trifluoride is used in molar excess to the amount of promoter. This can be accomplished by using a closed reactor and maintaining a positive boron trifluoride pressure over the reaction mixture. The promoter can be mixed with the olefin feed and the reaction can be carried out in a batch or continuous process at temperatures of about 0° to 200° C. and pressures ranging from atmospheric up to, for example, 1,000 psig. The reaction temperature will change the oligomer distribution, with increasing temperatures favoring the production of dimers. Preferred reaction temperatures and pressures are about 20° to 90° C. and 5 to 100 psig.

When a desired oligomer distribution is reached, the reaction is terminated by venting off excess boron trifluoride gas and purging with nitrogen gas to replace all boron trifluoride gaseous residue. The reaction product, unreacted monomer, and boron trifluoride-promoter complex residue are removed from the reactor for further processing. Some promoters can cause an undesirable emulsion layer formed between the reactor product and the boron trifluoride-promoter complex. Generally this emulsion has a higher viscosity than the reactor product and can form a coating on the walls of the reactor and transfer lines.

The reactor product is then washed with an aqueous caustic solution and followed by several water washes to ensure neutralization. During the decanting steps, an emulsion layer at the organic and aqueous interface can be detected with some of the catalytic promoters. This can cause ineffective separation of the product from wash solutions and other operating difficulties such as equipment corrosion and plugging. Some primary promoters, such as 4-hydroxy-4-methyl-2-pentanone, do not form any emulsions in either the reactor or the water wash. In contrast, prior art promoters, such as alcohol alkoxylates, (U.S. Pat. Nos. 5,068,487, 5,171,918 and 5,171,905) form emulsions in both the reactor and water wash.

The oligomer mixture from the reaction contains monomer, which can be removed by distillation. The monomer has been found to contain appreciable amounts of less reactive, isomerized material. However, this monomer can be recycled because it will react to form oligomers in the presence of fresh α-olefin monomer. For example, portions of up to about 25 wt. %, and preferably 5 to 15 wt. % recycled monomer, based on total monomer, can be mixed with fresh monomer. The product mixture can be further separated by distillation to provide one or more product fractions having the desired viscosities for use in various lubricant applications such as drilling, hydraulic or metal working fluids, gear oils and crankcase lubricants.

The oligomer product can be hydrogenated by conventional methods to increase the oxidation stability of the product. Supported nickel catalysts are useful. For example, nickel on a Kieselguhr support gives good results. Batch or continuous processes can be used. For example, the catalyst can be added to the liquid and stirred under hydrogen pressure or the liquid may be trickled through a fixed bed of the supported catalyst under hydrogen pressure. Hydrogen pressures of about 100 to 1,000 psig at temperatures of about 150° to 300° C. are especially useful.

EXAMPLES

The invention will be further illustrated by following examples, which set forth particularly advantageous method embodiments. While the Examples are provided to illustrate the present invention, they are not intended to limit it.

Examples 1 through 4 show the improvement in dimer yield using the promoters of the present invention. Example 1 is a comparative example showing batch oligomerization of 1-octene using BF$_3$-butanol. Examples 2 through 4 are examples of the present invention. Note that the final dimer to trimer and higher oligomer ratio for the present invention are in the range of from 0.64:1 to 1.33:1, which are all at least twice as high as the ratio for the comparative example.

COMPARATIVE EXAMPLE 1

BF$_3$ AND BUTANOL

The oligomerization reaction was carried out in an autoclave reactor. The reactor was equipped with a packless stirrer, and all wetted surfaces were made of 316 stainless steel. The reactor had an external electrical heater and an internal cooling coil for temperature control. The reactor was equipped with a dip tube, gas inlet and vent valves, and a pressure relief rupture disc. Prior to the monomer charge, the reactor was cleaned, purged with nitrogen and tested for leaks.

One thousand-grams of 1-octene was charged into the reactor. As shown in Table 1, butanol, as the promoter, was added to a concentration of 0.25 wt. % based on feed. The entire reactor content was heated under a nitrogen blanket to reach 75° C. When the reactor temperature reached equilibrium, the reactor was evacuated to remove the nitrogen. Boron trifluoride gas was then sparged slowly with agitation in addition to cooling water circulating through the reactor cooling coil to avoid reactor temperature overrun. Additional boron trifluoride was added as necessary to maintain a reactor pressure of 20 psig. Small representative fluid samples were taken at 15, 30 and 60 minutes for gas chromatographic analysis. The reaction was terminated after two hours by venting off excess boron trifluoride gas and purging with nitrogen gas to replace all boron trifluoride gaseous residue. The reaction product and unreacted monomer were removed from the reactor. The reactor product was then washed with a 4 wt. % aqueous sodium hydroxide solution followed by several water washes to ensure neutralization. During the wash steps, an emulsion layer at the organic and aqueous interface was observed when using some of the promoters. The oligomer distribution of the final product was analyzed by gas chromatography. Reaction times and product analyses are given in Table 1.

GAS CHROMATOGRAPHY METHOD

Hewlett-Packard Model 5710A gas chromatograph is used to analyze oligomer distribution of product samples in all the examples presented. The instrument had a 1/8×30-inch stainless steel packed column that contains Chromosorb PAW 80/100 mesh packing with 5% Dexsil 300 coating. The instrument was set up in the following oven temperature profile:
- Initial temperature—150° C.
- Ramp up rate—16° C. per minute
- Final temperature—400° C.
- Final time—16 minutes
- Post temperature—100° C.
- Post time—3 minutes

EXAMPLE 2

BF$_3$ AND 4-HYDROXY-4-METHYL-2-PENTANONE

The process of Example 1 was repeated except that the promoter was 4-hydroxy-4-methyl-2-pentanone. Reaction times and product analyses are given in Table 1.

EXAMPLE 3

BF$_3$ AND 1-HYDROXY-2-BUTANONE

The process of Example 1 was repeated except that the promoter was 1-hydroxy-2-butanone. Reaction times and product analyses are given in Table 1.

EXAMPLE 4

BF$_3$ AND HYDROXY ACETONE

The process of Example 1 was repeated except that the promoter was hydroxy acetone. Reaction times and product analyses are given in Table 1.

EXAMPLE 5

BF$_3$ AND 3-HYDROXY-3-METHYL-2-BUTANONE

The process of Example 1 was repeated except that the promoter was 3-hydroxy-3-methyl-2-butanone. Reaction times and product analyses are given in Table 1.

EXAMPLE 6

BF$_3$ AND 3-HYDROXY-2-BUTANONE

The process of Example 1 was repeated except that the promoter was 3-hydroxy-2-butanone. Reaction times and product analyses are given in Table 1.

TABLE 1

Improvement In Dimer Yield Using The Promoters Of The Present Invention (1-octene)

| Example | Time (minutes) | Dimer (wt. %) | Trimer (wt. %) | Monomer Conversion (wt. %) | Calc. Visc. @ 100 C (cSt) | Dimer/ Trimer+ |
| --- | --- | --- | --- | --- | --- | --- |
| 1* | 30 | 24.6 | 46.9 | 94.3 | 1.99 | 0.35 |
|    | 120 | 21.9 | 47.7 | 96.7 | 2.09 | 0.29 |
| 2  | 30 | 23.8 | 13 | 37.6 | 1.34 | 1.72 |
|    | 120 | 52.7 | 33.1 | 93.9 | 1.50 | 1.28 |
| 3  | 30 | 45.6 | 38 | 91.6 | 1.54 | 0.99 |
|    | 120 | 42.1 | 41.1 | 95.7 | 1.64 | 0.79 |
| 4  | 30 | 43.4 | 39.3 | 93.8 | 1.62 | 0.86 |
|    | 120 | 37.6 | 41.5 | 96.0 | 1.75 | 0.64 |
| 5  | 30 | 54.6 | 30.3 | 94.0 | 1.48 | 1.38 |
|    | 120 | 51.1 | 32.8 | 95.7 | 1.55 | 1.15 |
| 6  | 30 | 59.6 | 25.8 | 89.8 | 1.34 | 1.97 |
|    | 120 | 54.3 | 26.9 | 95.2 | 1.51 | 1.33 |

*Comparative Example

Examples 7 through 9 show the use of secondary promoters with the promoters of the present invention.

EXAMPLE 7

BF$_3$, 4-HYDROXY-4-METHYL-2-PENTANONE, AND METHANOL

The process of Example 1 was repeated except that the promoter was 4-hydroxy-4-methyl-2-pentanone, and methanol was used in addition to the primary promoter. The amount of secondary promoter used was 0.05 wt. % based on feed. Reaction time and product analyses are given in Table 2.

EXAMPLE 8

BF$_3$, 1-HYDROXY-2-BUTANONE, AND METHYL-ETHYL-KETONE

The process of Example 1 was repeated except that the promoter was 1-hydroxy-2-butanone, and methyl-ethyl-ketone was used in addition to the primary promoter. The amount of secondary promoter used was 0.5 wt. % based on feed. Reaction time and product analyses are given in Table 2.

EXAMPLE 9

BF₃, HYDROXY ACETONE, AND METHYL-ETHYL-KETONE

The process of Example 1 was repeated except that the promoter was hydroxy acetone, and methyl-ethyl-ketone was used in addition to the primary promoter. The amount of secondary promoter used was 0.5 wt. % based on feed. Reaction time and product analyses are given in Table 2.

TABLE 2

Use Of Secondary Promoters (1-octene)

| Example | Time (minutes) | Dimer (wt. %) | Trimer (wt. %) | Monomer Conversion (wt. %) | Calc. Visc. @ 100 C (cSt) | Dimer/Trimer+ |
|---|---|---|---|---|---|---|
| 7 | 30 | 46.9 | 36.2 | 88.4 | 1.49 | 1.13 |
|   | 120 | 38.7 | 42.4 | 96.8 | 1.74 | 0.67 |
| 8 | 30 | 52.7 | 32.7 | 94.2 | 1.51 | 1.27 |
|   | 120 | 37.4 | 36.1 | 95.8 | 1.80 | 0.64 |
| 9 | 30 | 51.4 | 34.7 | 95.1 | 1.51 | 1.18 |
|   | 120 | 35.2 | 37.3 | 96.0 | 1.83 | 0.58 |

Examples 10 through 12 show the improvement in dimer yield using the promoters of the present invention. Example 10 is a comparative example showing batch oligomerization of 1-decene using BF₃-butanol. Examples 11 and 12 are examples of the present invention. Note that the final dimer to trimer and higher oligomer ratio for the present invention are 1.41:1 and 1.49:1, which are both at least three times as high as the ratio for the comparative example.

COMPARATIVE EXAMPLE 10

BF₃ AND BUTANOL

The process of Example 1 was repeated except that one-thousand grams of 1-decene was charged to the reactor in place of 1-octene. In addition, the reactor pressure was maintained at 10 psig to favor dimer formation in this comparative example. The reaction times and product analysis are given in Table 3.

EXAMPLE 11

BF₃ AND 1-HYDROXY-2-BUTANONE

The process of Example 1 was repeated except that one-thousand grams of 1-decene was charged to the reactor in place of 1-octene, and except that the promoter was 1-hydroxy-2-butanone Reaction times and product analyses are given in Table 3.

EXAMPLE 12

BF₃ AND HYDROXY ACETONE

The process of Example 1 was repeated except that one-thousand grams of 1-decene was charged to the reactor in place of 1-octene, and except that the promoter was hydroxy acetone. Reaction times and product analyses are given in Table 3.

TABLE 3

Improvement In Dimer Yield Using The Promoters Of The Present Invention (1-decene)

| Example | Time (minute) | Dimer (wt. %) | Trimer (wt. %) | Monomer Conversion (wt. %) | Dimer/Trimer+ |
|---|---|---|---|---|---|
| 10* | 30 | 24.8 | 42.5 | 82.4 | 0.43 |
|    | 120 | 28.1 | 45.4 | 93.5 | 0.43 |
| 11 | 30 | 54.5 | 25.7 | 84.9 | 1.79 |
|    | 120 | 55 | 28.7 | 91.9 | 1.49 |
| 12 | 30 | 54.2 | 26.4 | 85.4 | 1.74 |
|    | 120 | 53.9 | 30.1 | 92 | 1.41 |

*Comparative Example

Examples 13 and 14 show the use of secondary promoters with the promoters of the present invention. Note that the final dimer to trimer and higher oligomer ratio for the present invention with secondary promoters is higher than ratios shown above without secondary promoters.

EXAMPLE 13

BF₃, 1-HYDROXY-2-BUTANONE, AND METHYL-ETHYL-KETONE

The process of Example 1 was repeated except that one-thousand grams of 1-decene was charged to the reactor in place of 1-octene, the promoter was 1-hydroxy-2-butanone, and methyl-ethyl-ketone was used in addition to the primary promoter. The amount of secondary promoter used was 0.5 wt. % based on feed. Reaction time and product analyses are given in Table 4.

EXAMPLE 14

BF₃, HYDROXY ACETONE, AND METHYL-ETHYL-KETONE

The process of Example 1 was repeated except that one-thousand grams of 1-decene was charged to the reactor in place of 1-octene, the promoter was hydroxy acetone, and methyl-ethyl-ketone was used in addition to the primary promoter. The amount of secondary promoter used was 0.5 wt. % based on feed. Reaction time, and product analyses are given in Table 4.

TABLE 4

Use Of Secondary Promoters (1-decene)

| Example | Time (minute) | Dimer (wt. %) | Trimer (wt. %) | Monomer Conversion (wt. %) | Dimer/Trimer+ |
|---|---|---|---|---|---|
| 13 | 30 | 74.2 | 13.7 | 88.50 | 5.19 |
|    | 120 | 62.9 | 20.7 | 94.90 | 1.97 |
| 14 | 30 | 66.5 | 13.0 | 80.60 | 4.72 |
|    | 120 | 66.0 | 20.4 | 94.70 | 2.30 |

Examples 15 through 17 show the use of a secondary promoter (methanol) with a promoter of the present invention (4-hydroxy-4-methyl-2-pentanone) in a continuous process.

EXAMPLES 15 THROUGH 17

BF₃, 4-HYDROXY-4-METHYL-2-PENTANONE, AND METHANOL

The oligomerization reaction was carried out continuously in a bolted closure autoclave reactor. The reactor was equipped with a packless stirrer; all wetted surfaces were made of 3 16 stainless steel. The reactor had an external electrical heater and an internal cooling coil for temperature control. The reactor was equipped with a dip tube, gas inlet and vent valves, and a pressure relief rupture disc.

The temperature was controlled to 75° C. The reactor pressure control was achieved through supplying gaseous boron trifluoride on demand at 20 psig. Feed streams of monomer and promoters were injected continuously into the reactor at prescribed rates using liquid metering pumps. The primary promoter, 4-hydroxy-4-methyl-2-pentanone, concentration was 0.42 wt. % of the monomer feed and the secondary promoter, methanol, concentration was 0.34 wt. % of the monomer feed. The monomer was 1-octene.

The reactor contains a stirred liquid phase and a vapor phase; the liquid level was controlled by means of a differential pressure cell through the effluent of liquid reactants. Thus the residence time of the reactants was controlled by the reactor liquid volume and monomer flow rate. The liquid reactant was discharged into a low pressure letdown tank. This promoter combination did not form an emulsion layer. The product stream was then led to a caustic wash pot for boron trifluoride-promoter complex removal. The unsaturated product (hydrocarbon) phase was decanted. The monomer feed rate and product analyses are given in Table 5.

TABLE 5

Use of BF₃, 4-Hydroxy-4-Methyl-2-Pentanone, and Methanol In a Continuous Process

| Example | Monomer Feed Rate, gm/hr | Dimer (wt. %) | Trimer (wt. %) | Monomer Conversion (wt. %) | Viscosity @ 100 C (cSt) |
|---|---|---|---|---|---|
| 15 | 4486 | 42.5 | 27.0 | 74.5 | 1.47 |
| 16 | 2567 | 43.1 | 34.8 | 83.7 | 1.55 |
| 17 | 1535 | 39.5 | 38.2 | 87.1 | 1.61 |

EXAMPLE 18

EMULSION TEST

An additional benefit of some hydroxy carbonyl promoters is its freedom from emulsions in both the reactor and the quench and wash stages. Generally, a promoter which is predisposed toward formation of emulsions will be troublesome in both of these process areas.

A simple laboratory test method was used to detect the presence of emulsions. The method combines, in a 125 ml separatory funnel, 15 ml of unquenched oligomer reactor product and 20 ml of 4 wt. % NaOH solution. The separatory funnel is shaken vigorously to mix the phases well and then they are allowed to separate by settling. The presence of an interfacial layer observable between the hydrocarbon and aqueous layers having a thickness greater than 2 mm and persisting longer than five minutes is evidence of a stable emulsion. Emulsions have been observed to also form with other bases including KOH and NH₄OH and the laboratory test may be varied to substitute these agents for NaOH.

This emulsion test was applied to various reactor products. Emulsions were not observed for runs when 1-hydroxy-2-butanone, 4-hydroxy-4-methyl-2-pentanone, or 3-hydroxy-3-methyl-2-butanone were used as promoter. Emulsions were observed for runs when hydroxy acetone, 2-butoxyethanol (comparative example), or 3-hydroxy-2-butanone were used as promoter.

While the present invention has been described with reference to specific embodiments, this application is intended to cover those various changes and substitutions that may be made by those skilled in the art without departing from the spirit and scope of the appended claims.

What is claimed is:

1. A process for making an oligomer comprising contacting an olefinic monomer with boron trifluoride and a compound selected from the group consisting of hydroxyalkyl ketone and hydroxyalkyl aldehyde, wherein the process is carried out at a temperature of from 0° to 200° C. and a pressure of from atmospheric up to 1,000 psig.

2. A process according to claim 1 wherein the compound is a hydroxyalkyl ketone.

3. A process according to claim 2 wherein the hydroxyalkyl group contains from 1 to 6 carbon atoms; and wherein the ketone group is selected from the group consisting of methyl ketone and ethyl ketone.

4. A process according to claim 3 wherein the hydroxyl group is attached to a tertiary carbon.

5. A process according to claim 3 wherein the ketone is selected from the group consisting of hydroxy acetone, 1-hydroxy-2-butanone, 3-hydroxy-2-butanone, 3-hydroxy-3-methyl-2-butanone, and 4-hydroxy-4-methyl-2-pentanone.

6. A process according to claim 5 wherein the ketone is 4-hydroxy-4-methyl-2-pentanone.

7. A process according to claim 1 wherein the olefinic monomer is a straight-chain, α-olefinic monomer containing from 6 to 20 carbon atoms.

8. A process according to claim 7 wherein the olefinic monomer contains from 6 to 12 carbon atoms.

9. A process according to claim 8 wherein the oligomer product has a kinematic viscosity at 100° C. of less than 3.6 cSt.

10. A process according to claim 8 wherein the olefinic monomer contains 8 to 10 carbon atoms.

11. A process according to claim 10 wherein the oligomer product has a kinematic viscosity at 100° C. of less than 2.0 cSt.

12. A process according to claim 11 wherein the oligomer product has a kinematic viscosity at 100° C. of less than 1.7 cSt.

13. A process according to claim 1 wherein the oligomer product comprises dimer and trimer of said monomer, wherein the ration of dimer to the sum of trimer and higher oligomer is at least 0.5:1, and wherein the oligomer product contains at least 70 wt. % dimer and trimer before removal of unreacted monomer.

14. A process according to claim 13 wherein the oligomer product contains at least 80 wt. % dimer and trimer before removal of unreacted monomer.

15. A process according to claim 14 wherein the ratio of dimer to the sum of trimer and higher oligomer is at least 1:1, and wherein the oligomer product is at least 90 wt. % dimer and trimer before removal of unreacted monomer.

16. A process according to claim 1 wherein the oligomer product is hydrogenated.

17. A process for making an oligomer comprising contacting an olefinic monomer with:

(a) boron trifluoride,
(b) a compound selected from the group consisting of hydroxyalkyl ketone and hydroxyalkyl aldehyde, and
(c) a promoter selected from the group consisting of aldehydes, alcohols, alcohol alkoxylates, carboxylic acids, ethers, ketones, and their mixtures wherein the process is carded out at a temperature of from 0° to 200° C. and a pressure of from atmospheric up to 1,000 psig.

18. A process according to claim 17 wherein the alcohol is methanol.

* * * * *